United States Patent [19]

Kehr et al.

[11] Patent Number: 4,593,032

[45] Date of Patent: Jun. 3, 1986

[54] TERGURIDE AS ANTIHYPERTENSIVE

[75] Inventors: Wolfgang Kehr; Gertrud Schröder; Gunter Stock; Helmut Wachtel, all of Berlin, Fed. Rep. of Germany

[73] Assignee: Schering Aktiengesellschaft, Berlin and Bergkamen, Fed. Rep. of Germany

[21] Appl. No.: 712,064

[22] Filed: Mar. 15, 1985

[30] Foreign Application Priority Data

Mar. 16, 1984 [DE] Fed. Rep. of Germany ....... 3410218

[51] Int. Cl.$^4$ ............................................ A61K 31/44
[52] U.S. Cl. ................................................... 514/288
[58] Field of Search ....................................... 514/288

[56] References Cited

FOREIGN PATENT DOCUMENTS 2238540 2/1973 Fed. Rep. of Germany .
3129714A1 2/1983 Fed. Rep. of Germany .

OTHER PUBLICATIONS

Cavero, et al., Life Sciences 31:939–948, 1059–1069 (1982).
Stumpe et al., Lancet 2:211 (1977).

*Primary Examiner*—Stanley J. Friedman
*Attorney, Agent, or Firm*—Millen & White

[57] ABSTRACT

Terguride and its physiologically compatible salts have been discovered to be useful in the treatment of essential hypertonia, e.g., in humans, e.g., in doses of 0.1–1.0 mg/day.

8 Claims, No Drawings

TERGURIDE AS ANTIHYPERTENSIVE

BACKGROUND OF THE INVENTION

This invention relates to a new use for terguride.

Terguride [3-(6-methylergolin-8α-yl)-1,1-diethyl urea] itself is known, as are its nidation- and lactation-inhibiting as well as antipsychotic effects upon oral administration to animals and to human patients. These effects are based on its partially agonistic action on dopamine receptors (German Pat. No. 2,238,540, DOS No. 3,129,714).

Suitable physiologically compatible salts of terguride include those with inorganic and organic acids. Usable for salt formation are, for example, hydrochloric acid, phosphoric acid, sulfuric acid, methanesulfonic acid, glucoheptanoic acid, succinic acid, tartaric acid, maleic acid, etc. A preferred salt is terguride dihydrogen phosphate.

It is known that dopamine agonists lead to lowering of the blood pressure, on the one hand, via direct dilation of the blood vessels and, on the other hand, via reduced release of noradrenalin from sympathetic nerve endings (Cavero, I. et al., Life Science 31: 939–948 and 1059–1069 [1982]). For this reason, dopamine agonists, such as various ergot alkaloids, e.g. bromocriptine or lisuride, have been utilized in human medicine for hypertension therapy (Stumpe, K. O., Kolloch, R., Higuchi, M. K., Kruck, F., Vetter, H.: Hperprolactinemia and Antihypertensive Effect of Bromocriptine in Essential Hypertension", Lancet 2 : 211, 1977).

These compounds, however, have the drawback that the undesirable side effect of vomiting is to be expected because of simultaneous stimulation of the dopamine receptors in the area postrema.

SUMMARY OF THE INVENTION

Accordingly, it is an object of the present invention to make available an antihypertensive medicine which overcomes these disadvantages.

Upon further study of the specification and appended claims, further objects and advantages of this invention will become apparent to those skilled in the art.

These objects have been achieved based on the finding that terguride has antihypertensive activity without triggering emetic side effects.

DETAILED DISCUSSION

In pharmacological tests on animals, terguride displayed dose-dependent lowering of the blood pressure in spontaneously hypertensive rats, prepared by a method modified in accordance with Weeks (Weeks, J. R., Routine Direct Measurement of Arterial Pressure in Unanesthetized Rats, Proc. S. Exp. Biol. Med. 104: 646–648, 1960).

The following pharmacological tests were conducted to examine antihypertensive activity and its dependence on the dose:

The medium arterial, the systolic and the diastolic blood pressures were determined by means of an implanted aorta catheter in male SH rats weighing about 300 g. Terguride was administered in a dosage of 200 μg/kg body weight (BW) in the form of a bolus via a catheter placed in the vena jugularis. The dopamine antagonist haloperidol (1 mg/kg i.p.) was administered 45 minutes before intravenous injection of terguride.

In the dose utilized, terguride causes biphasic lowering of the blood pressure, which can be antagonized to the largest part by the previous administration of haloperidol.

Male SH rats prepared as indicated above each received 10, 75, 150 or 225 μg/kg BW of terguride. A dose-dependent lowering of the blood pressure was effected by terguride, the maximum of which is reached as early as at 150 μg/kg BW. By increasing the dose to 225 μg/kg BW, only a marginal prolongation of the markedly antihypertensive phase could be observed. The maximum lowering of the blood pressure was about 28–30% of the initial value. This level was attained about 20 minutes after administration.

Cardiac frequency is increased by terguride in dependence on the dose. This increase fades as early as 13 minutes after administration and lies chronologically before the maximum drop in blood pressure. Furthermore, the effect of terguride on the cardio- and hemodynamics was studied on normotensive, male rats weighing about 300 g. The animals were anesthetized with 70–100 mg/kg BW of Na phenobarbital i.p. For blood pressure measurements, a catheter was inserted in the abdominal aorta via the A. femoralis. The injection catheter for the test compound was placed in the right V. femoralis. Via a catheter in the left ventricle, the ventricle pressure could be recorded, deriving therefrom $dp/dt_{max}$. The cardiac output per minute was determined by the refrigeration dilution method. Cardiac frequency was determined from the EKG graph (derived in the cardiac axis). A short-term drop in medium arterial blood pressure lasting for about 5 minutes was experienced by anesthetized animals with 150 μg/kg BW of terguride. Maximum reduction amounts of approximately 40% of the starting value. Peripheral resistance drops initially by about 40% of the starting value and rises after only 5 minutes again to 75% of the starting value. Cardiac frequency is not affected. Simultaneously with the blood pressure, $dp/dt_{max}$ is decreased, which can be explained by afterload reduction caused by blood pressure.

A further investigation, directed to the $\alpha_1$-adrenolytic and directly vasodilating activity of terguride, was conducted on isolated, spirally cut strips of rat aorta by affecting, with $10^{-10}$ to $3 \times 10^{-5}$ mole/l of terguride, a contraction induced with $10^{-7}$ mole of noradrenalin/l of bath liquid, according to the method by Furchgott (Furchgott, R. F., Bhadrakon S., Reactions of Strips of Rabbit Aorta to Epinephrine, Isopropylarterenol, Sodium Nitrite and Other Drugs, J. Pharmacol. 108: 129–143, 1953). The method of Arunlakshana and Schild (Arunlakshana, O., Schild, H. O.: Some Quantitative Uses of Drug Antagonists, Brit. J. Pharmacol. 14: 48–58 [1959]) was used to determine the $\alpha_1$-adrenolytic strength of activity (determination of the $pA_2$ value). A directly vasodilating property was examined on $K^+$-depolarized strips of rat aorta.

Terguride shifts the noradrenalin dose effect curve in parallel toward the right, so that the $pA_2$ value for terguride is 7.99. However, an influence on the contradiction in $K^-$-depolarized aorta strips, after addition of terguride, could not be found.

The results of circulatory-pharmacological tests conducted on animals admit of the conclusion that terguride causes lowering of the blood pressure by way of a dopamine-agonistic activity. The α-adrenolytic effects, in contrast thereto, contribute only insubstantially toward lowering of the blood pressure.

The dopamine-agonistically effective quality was confirmed in a human-pharmacological crossover study on 15 normotonic test subjects; inter alia, reduction in prolactin was employed as a parameter for dopamine-agonistic activity. The plasma prolactin levels were lowered, in dependence on the dose, after a one-time oral administration of 0.2, 0.5 and 1.0 mg of terguride, up to 24 hours after administration. In two of 15 normotonic test subjects, orthostatic drop in blood pressure and slight nausea were observed, only after 1 mg of terguride. Otherwise, blood pressure and cardiac frequency of these test subjects were not impaired.

In analogy to the finding obtained in animal experiments, it can be seen that terguride is a drug that brings about lowering of the blood pressure, based on dopamine-agonistic activity, in hypertensive patients but not in normotensive patients; cumulative triggering of emesis does not occur in the blood-pressure-lowering range. Terguride is, accordingly, a useful new agent for treatment of essential (idiomatic) hypertension in patients.

As in conventional medical practice, terguride or its pharmacological salts can be administered subcutaneously, intramuscularly, intravenously and preferably, per os, analogously to its administration for conventional purposes. The daily dosage is generally 0.1–1.0 mg, preferably 0.1–0.5 mg, typically 0.2 and 0.4 mg. Moreover, the administration of terguride as as an antihypertensive is analogous to the administration of conventional antihypertensives, e.g., prazosin.

The medical specialties of this invention are fully conventionally prepared for administration to mammals, including humans, by processing terguride with excipients, diluents, flavoring agents, etc., customary in pharmacy. Especialy suitable for injections are aqueous, but also oily solutions, as well as suspensions. For the production of intramuscular time-release versions, the active agents can be suspended or dissolved in fatty oils, according to conventional methods.

The medicinal agents of this invention are suitable for oral administration, in particular, in the form of tablets, capsules, dragees, pills, suspensions and solutions. However, depot forms for oral administration are also suitable, which are obtained, for example, by adding hydrogenated fats and by processing with resinogenous compounds and lacquers. Drops for oral administration can be provided by aqueous solutions or suspensions of the active compound in oils with the addition of flavoring agents and/or solubilizers.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of achieving an antihypertensive effect in a patient comprising administering to a patient suffering from hypertension an antihypertensively effective amount of terguride or a pharmacologically acceptable acid salt thereof.

2. A method of claim 1 wherein the amount of terguride is 0.1–1.0 mg/day.

3. A method of claim 1 wherein the administration is orally.

4. A method of claim 1 wherein the administration is subcutaneously, intramuscularly or intravenously.

5. A method of claim 1 comprising administering terguride.

6. A method of claim 1 comprising administering a pharmacologically acceptable salt of terguride.

7. A method of claim 3 wherein terguride or a salt thereof is administered as a tablet, capsule, dragee, pill, suspension or solution.

8. A method of treating idiomatic hypertonia in a patient with substantially no emesis as a side effect comprising administering to the patient an antihypertensively effective amount of terguride or a pharmacologically acceptable salt thereof.

* * * * *